United States Patent
Meliniotis et al.

(10) Patent No.: US 10,188,810 B2
(45) Date of Patent: Jan. 29, 2019

(54) INHALER

(71) Applicant: VECTURA DELIVERY DEVICES LIMITED, Chippenham (GB)

(72) Inventors: Andreas Meliniotis, Cambridge (GB); Stephen Eason, Cambridge (GB); Roger Clarke, Cambridge (GB); Liam McGuinness, Cambridge (GB)

(73) Assignee: VECTURA DELIVERY DEVICES LIMITED, Chippenham (GB)

(*) Notice: Subject to any disclaimer, the term of this patent is extended or adjusted under 35 U.S.C. 154(b) by 841 days.

(21) Appl. No.: 14/608,125

(22) Filed: Feb. 11, 2015

(65) Prior Publication Data
US 2015/0209531 A1    Jul. 30, 2015

Related U.S. Application Data
(63) Continuation-in-part of application No. 13/885,778, filed as application No. PCT/GB2011/052338 on Nov. 25, 2011, now abandoned.

(30) Foreign Application Priority Data

Nov. 26, 2010  (GB) .................................. 1020130.9
Jun. 7, 2011   (GB) .................................. 1109493.5
Aug. 31, 2011  (GB) .................................. 1115000.0

(51) Int. Cl.
*A61M 15/00*   (2006.01)
*A61M 15/08*   (2006.01)

(52) U.S. Cl.
CPC .... *A61M 15/0058* (2014.02); *A61M 15/0021* (2014.02); *A61M 15/0026* (2014.02);
(Continued)

(58) Field of Classification Search
CPC .......... A61M 15/0058; A61M 15/0081; A61M 15/0026; A61M 15/0021; A61M 15/0056;
(Continued)

(56) References Cited

U.S. PATENT DOCUMENTS

| 5,860,419 A | 1/1999 | Davies et al. |
| 5,921,237 A | 7/1999 | Eisele et al. |

(Continued)

FOREIGN PATENT DOCUMENTS

| EP | 2082770 A1 | 7/2009 |
| EP | 2082771 A1 | 7/2009 |

(Continued)

OTHER PUBLICATIONS

Search Report from the Intellectual Property Office of the United Kingdom, dated Sep. 28, 2011, issued in connection with corresponding British Application No. GB1109493.5.

(Continued)

*Primary Examiner* — Timothy Stanis
(74) *Attorney, Agent, or Firm* — Davidson, Davidson & Kappel, LLC

(57) ABSTRACT

An inhaler comprising a housing defining a chamber to receive a strip having a plurality of blisters each containing a dose of medicament for inhalation by a user is disclosed. It comprises an actuating lever and a blister strip drive member rotatably mounted in the chamber to sequentially move each blister into a blister opening position. The blister strip drive member and the actuating lever comprise a drive gear and a drive gear element, respectively, that cooperate to effect rotation of the blister strip drive member in response to rotation of the actuating lever. The drive gear and drive gear element are disposed on the outside of the housing remote from the chamber.

5 Claims, 16 Drawing Sheets

(52) U.S. Cl.
CPC .... *A61M 15/0033* (2014.02); *A61M 15/0045* (2013.01); *A61M 15/0051* (2014.02); *A61M 15/0056* (2014.02); *A61M 15/0081* (2014.02); *A61M 15/08* (2013.01)

(58) Field of Classification Search
CPC .......... A61M 15/0051; A61M 15/0033; A61M 15/0045
See application file for complete search history.

(56) References Cited

U.S. PATENT DOCUMENTS

| | | |
|---|---|---|
| 6,880,722 B2 | 4/2005 | Anderson et al. |
| 2005/0172964 A1 | 8/2005 | Anderson et al. |
| 2005/0228241 A1 | 10/2005 | McNair |
| 2005/0228341 A1 | 10/2005 | Edgerley |
| 2005/0247306 A1 | 11/2005 | Harvey et al. |
| 2007/0154407 A1 | 7/2007 | Peters et al. |
| 2007/0267015 A1 | 11/2007 | Thoemmes et al. |
| 2008/0196718 A1 | 8/2008 | Connell et al. |
| 2008/0202515 A1 | 8/2008 | Hodson et al. |
| 2008/0223366 A1 | 9/2008 | Davies et al. |
| 2009/0007907 A1 | 1/2009 | Eason et al. |
| 2009/0007908 A1* | 1/2009 | Eason ............... A61M 15/0045 128/203.15 |
| 2009/0188498 A1 | 7/2009 | Thoemmes et al. |
| 2009/0314291 A1 | 12/2009 | Anderson et al. |
| 2010/0083962 A1 | 4/2010 | Von Schuckmann |
| 2010/0242960 A1 | 9/2010 | Wolfgang |
| 2010/0258118 A1 | 10/2010 | Morton |
| 2010/0288278 A1 | 11/2010 | Pocock et al. |
| 2011/0226244 A1 | 9/2011 | Perkins et al. |
| 2011/0308516 A1 | 12/2011 | Price et al. |

FOREIGN PATENT DOCUMENTS

| | | |
|---|---|---|
| EP | 2082772 A1 | 7/2009 |
| EP | 2239001 | 10/2010 |
| GB | 2407042 | 4/2005 |
| JP | H04220266 | 8/1992 |
| JP | 2005506154 | 3/2005 |
| JP | H05074547 | 3/2005 |
| JP | 2005523773 | 8/2005 |
| JP | 2005532091 | 10/2005 |
| JP | 2006527046 | 11/2006 |
| JP | 2010532191 | 10/2010 |
| WO | WO0108732 | 2/2001 |
| WO | WO 02/24263 | 3/2002 |
| WO | WO 2003/013633 A1 | 2/2003 |
| WO | WO03035151 | 5/2003 |
| WO | WO 03/090811 | 11/2003 |
| WO | WO03092575 | 11/2003 |
| WO | WO03095010 | 11/2003 |
| WO | WO 2005/016424 | 2/2005 |
| WO | WO 2005/037353 | 4/2005 |
| WO | WO 2007/012871 | 2/2007 |
| WO | WO 2008/078034 | 3/2008 |
| WO | WO 2009/003989 | 1/2009 |
| WO | WO 2009/007352 | 1/2009 |
| WO | WO 2009/092594 | 7/2009 |
| WO | WO 2009/092652 | 7/2009 |
| WO | WO 2009/092768 | 7/2009 |
| WO | WO 2009/092770 A1 | 7/2009 |
| WO | WO 2009/132791 | 11/2009 |
| WO | WO 2010/040779 | 4/2010 |
| WO | WO 2011/049541 | 4/2011 |

OTHER PUBLICATIONS

Search Report from the Intellectual Property Office of the United Kingdom, dated Sep. 12, 2012, issued in connection with corresponding British Application No. GB1209263.1.

Search Report from the Intellectual Property Office of the United Kingdom, dated Dec. 13, 2011, issued in connection with corresponding British Application No. GB1115000.0.

International Search Report issued in corresponding GB Application No. International Application No. PCT/GB11/052338, dated May 25, 2012.

Office Action dated May 29, 2014 issued in commonly-owned U.S. Appl. No. 13/222,008.

* cited by examiner

INHALER

This application is a continuation of U.S. patent application Ser. No. 12/864,527, filed on Jul. 26, 2010, which is a national phase application under 35 U.S.C. 371 of International Application No. PCT/GB11/052338, filed Nov. 25, 2011, which claims priority to GB 1020130.9, filed on Nov. 26, 2010, and GB 1109493.5, filed on Jun. 7, 2011, and GB 1115000.0, filed on Aug. 31, 2011; the disclosures of which are all hereby incorporated by reference herein.

CROSS-REFERENCE TO RELATED APPLICATIONS

U.S. application Ser. No. 13/222,008 (now issued as U.S. Pat. No. 8,931,480) is hereby incorporated by reference in its entirety.

FIELD OF INVENTION

The present invention relates to an inhalation device for oral or nasal delivery of medicament in powdered form. More specifically, the invention relates to an inhaler having a housing to receive a strip having a plurality of blisters spaced along the length of the strip, each blister having a puncturable lid and containing a dose of medicament for inhalation by a user. The invention also relates to an inhaler containing a strip of blisters each having a puncturable lid and containing a dose of medicament for inhalation by a user of the device according to the invention.

BACKGROUND OF THE INVENTION

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have more recently also been used to deliver drugs to the bloodstream via the lungs, thereby avoiding the need for hypodermic injections.

It is common for dry powder formulations to be pre-packaged in individual doses, usually in the form of capsules or blisters which each contain a single dose of the powder which has been accurately and consistently measured. A blister is generally cold formed from a ductile foil laminate or a plastics material and includes a puncturable lid which is permanently heat-sealed around the periphery of the blister during manufacture and after the dose has been introduced into the blister. A foil blister is preferred over capsules as each dose is protected from the ingress of water and penetration of gases such as oxygen in addition to being shielded from light and UV radiation all of which can have a detrimental effect on the delivery characteristics of the inhaler if a dose becomes exposed to them. Therefore, a blister offers excellent environmental protection to each individual drug dose.

Inhalation devices that receive a blister pack comprising a number of blisters each of which contain a pre-metered and individually packaged dose of the drug to be delivered are known. Actuation of the device causes a mechanism to breach or rupture a blister, such as by puncturing it or peeling the lid off, so that when the patient inhales, air is drawn through the blister entraining the dose therein that is then carried out of the blister through the device and via the patient's airway down into the lungs. Pressurized air or gas or other propellants may also be used to carry the dose out of the blister. Alternatively, the mechanism that punctures or opens the blister may push or eject the dose out of the blister into a receptacle from which the dose may subsequently be inhaled.

It is advantageous for the inhaler to be capable of holding a number of doses to enable it to be used repeatedly over a period of time without the requirement to open and/or insert a blister into the device each time it is used. Therefore, many conventional devices include means for storing a number of blisters each containing an individual dose of medicament. When a dose is to be inhaled, an indexing mechanism moves a previously emptied blister away from the opening mechanism so that a fresh one is moved into a position ready to be opened for inhalation of its contents.

An inhaler of the type described above is known from the Applicant's own co-pending international application that has been published as WO2005/037353 A1.

According to one embodiment described and claimed in WO 2005/037353 A1, and illustrated in FIGS. 1 and 2 of the accompanying drawings, an inhaler 1 has a housing 2 containing a coiled strip of blisters 3. An indexing mechanism 4 comprising a single actuating lever 5 unwinds the coil 3 one blister at a time so that they pass over a blister locator chassis 6 and successively through a blister piercing station 7, when the actuator 5 is pivoted in a direction indicated by arrow "A" in FIG. 2. The blister 3a located at the blister piercing station 7 on each movement of the actuator 5 is pierced on the return stroke of the actuator 5 (in the direction indicated by arrow "B" in FIG. 2) by piercing elements 8 on the actuator 5 itself so that, when a user inhales through a mouthpiece 9, an airflow is generated within the blister 3a to entrain the dose contained therein and carry it out of the blister 3a via the mouthpiece 9 and into the user's airway.

The device known from WO2005/037353 A1 has already been modified so as provide a fully integrated device, i.e. one in which the used blisters are retained within its housing so that a user never has to come into direct contact with the blister strip. In one modified embodiment, known from the Applicant's own previous application that has now been published as WO09/007352 A1, there is provided a flexible and resilient spiral element mounted within the housing of the device into which the used portion of the blister strip is directed so that, as the strip is gradually used up, the spiral expands as more and more of the strip is fed or pushed into it between its coils. The inhaler of the present invention, in its preferred form, is also a fully integrated device that retains the used blisters, although in a preferred embodiment it has a wall to separate the interior of the housing into used and unused blister compartments. The wall is preferably rigid and slideably mounted so that the size of the unused and used blister compartments changes relative to each other as the number of blisters that are used increases and the number of unused blisters decreases.

The aforementioned document also describes an embodiment in which used blisters are crushed between the blister strip drive or indexing wheel and the inner surface of the casing of the device, which is also a feature of the inhaler of the present invention. As crushing takes place as the used strip passes around the blister strip drive member, a curl or curved form is imparted to the strip which helps it to coil up within the chamber.

The inhaler of the invention may also incorporate a blister strip drive mechanism or indexing mechanism that forms the subject of the Applicant's own previous international application that has now published as WO2009/092652 A1.

The disclosures of WO2005/037353 A1, WO09/007352 A1 and WO2009/092652 A1 are all incorporated herein by reference.

SUMMARY OF THE INVENTION

The present invention seeks to provide another inhalation device of the type disclosed in the above-mentioned applications, and which also has a relatively simple construction, is robust, straightforward to manufacture and easy for the patient to use.

According to the invention, there is provided an inhaler comprising a housing defining a chamber to receive a strip having a plurality of blisters each containing a dose of medicament for inhalation by a user, an actuating lever, and a blister strip drive member rotatably mounted in the chamber to sequentially move each blister into a blister opening position, wherein the blister strip drive member and the actuating lever comprise a drive gear and a drive gear element, respectively, that cooperate to effect rotation of the blister strip drive member in response to rotation of the actuating lever, said drive gear and drive gear element being disposed on the outside of the housing remote from the chamber. This has the advantage that the drive gear and drive gear element are isolated from any residual powder that may be deposited within the chamber.

The inhaler may comprise a mouthpiece through which a dose of medicament can be inhaled and a cap pivotally mounted on the housing to cover the mouthpiece. The drive gear and drive gear element are preferably disposed between the housing and the cap so as to be enclosed by said cap. As the cap covers the drive gear and drive gear element, they are protected from ingress of dirt and are concealed from view and cannot be contacted by a person holding the device.

In a preferred embodiment, the housing has opposing side wall surfaces and the cap has portions that extend across respective side wall surfaces, said drive gear and drive gear element being disposed between one of said side wall surfaces and one of said cap portions.

In one embodiment, the drive gear of the blister strip drive member includes a shaft that extends through an aperture in a side wall surface of the housing, for coupling to the blister strip drive wheel.

Preferably, the actuating lever comprises an actuating button that extends across the outside of the housing between said opposing side wall surfaces of the housing, and a plate-like portion extending from each end of the actuating button across respective side wall surfaces on the outside of the housing, beneath said cap portions. In this embodiment, the drive gear element on the actuating lever is preferably formed on one of said plate-like portions. As the actuating lever is pivotally supported at two points, spaced from each other by the width of the housing, support for the lever is improved as opposed to it being mounted at only one point and it is more resistant to being twisted about an axis extending radially from its pivot axis.

Each plate-like portion of the actuating lever may be pivotally mounted to a respective side wall surface of the housing to pivotally mount the actuating lever to the outside of the housing remote from the chamber.

In a preferred embodiment, the inhaler comprises a piercing member that pivots in response to rotation of the actuating lever to puncture the lid of an aligned blister, wherein one of the actuating lever and the blister piercing member has a drive cam element and the other of the actuating lever and the blister piercing member has a drive cam surface, the drive cam element and the drive cam surface cooperating with each other in response to rotation of the actuating lever so that the blister piercing element pivots to puncture the lid of an aligned blister.

In a preferred embodiment wherein the piercing member pivots together with the mouthpiece, the mouthpiece being pivotally mounted to the housing such that the mouthpiece pivots to puncture the lid of an aligned blister in response to rotation of the actuating lever. In this embodiment, the mouthpiece may be pivotally mounted to the outside of the housing remote from the chamber.

Preferably, the mouthpiece has peripheral walls extending from opposing edges that extend across respective side wall surfaces on the outside of the housing remote from the chamber, said peripheral walls being pivotally mounted to said side wall surfaces of the housing. At least one of the drive cam element and drive cam surface may be formed in one of said peripheral walls.

Preferably, the drive cam element and drive cam surface are disposed beneath a cap portion.

BRIEF DESCRIPTION OF DRAWINGS

Embodiments of the invention will now be described, by way of example only, with reference to FIGS. 3 to 16 of the accompanying drawings, in which.

DETAILED DESCRIPTION OF THE INVENTION

Figure 3:
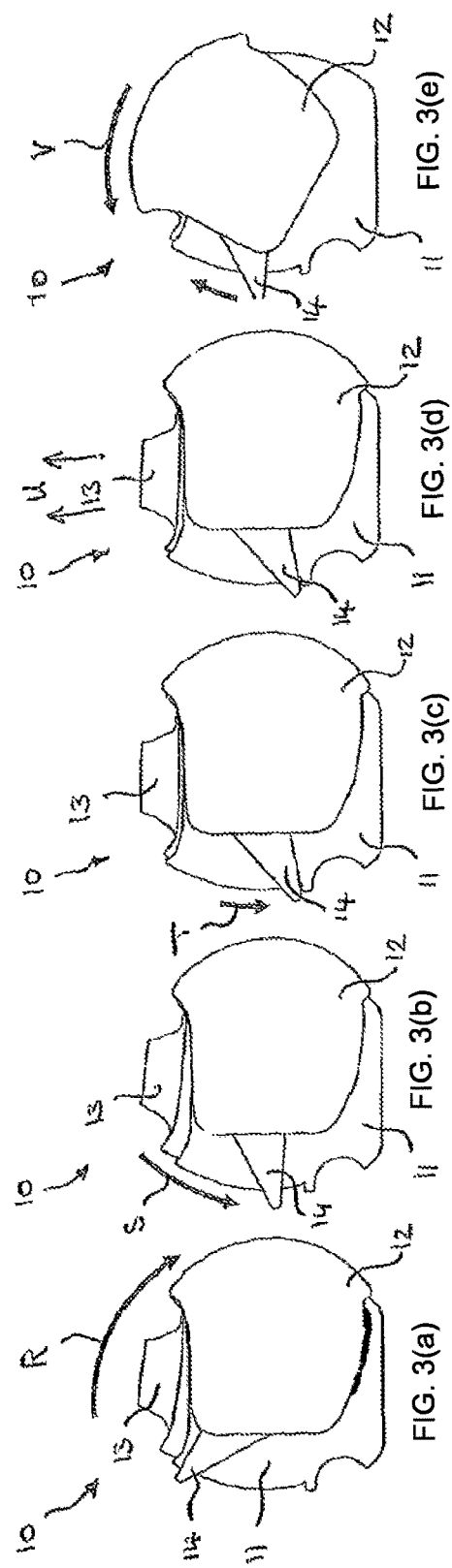
FIGS. 3*a* to 3*e* is a sequence of drawings to show the general function and operation of the inhaler according to the invention.
Figure 4:
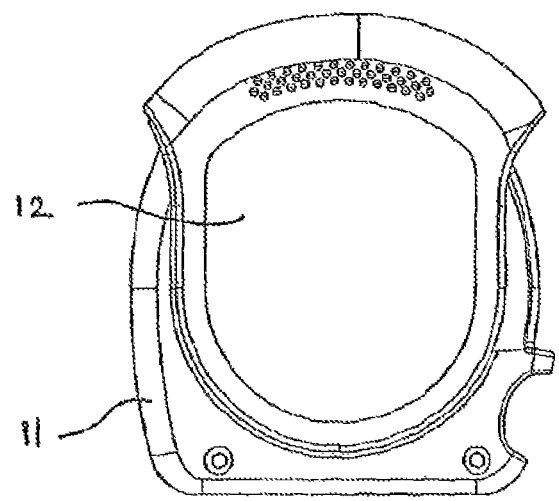
FIG. 4 is a side elevation of an inhalation device according to an embodiment of the invention.
Figure 5:
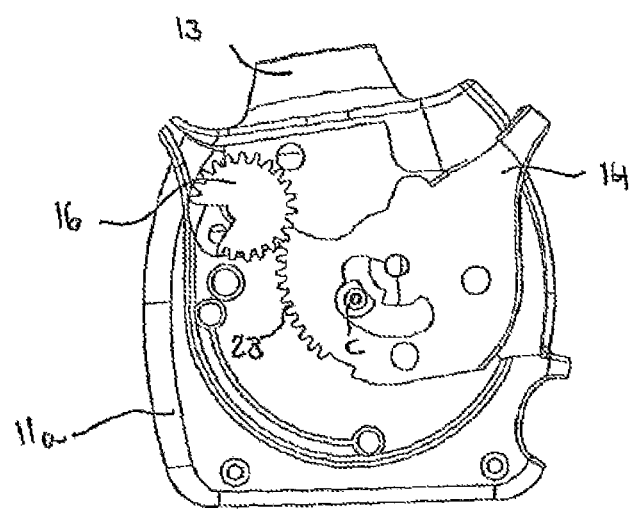
FIG. 5 is the side elevation of FIG. 4, but with the cap removed so that the internal components can be seen.
Figure 6:
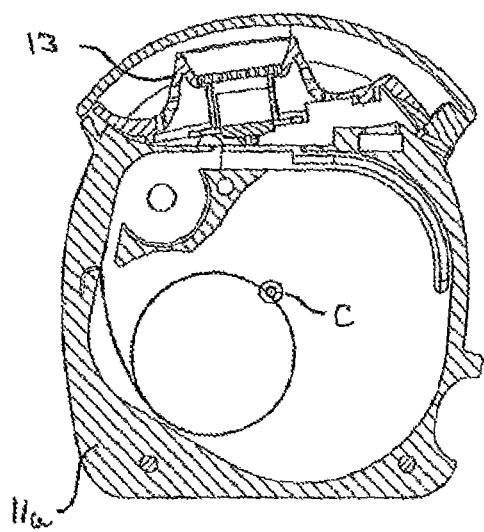
FIG. 6 is the side elevation of FIG. 5 after removal of one-half of the shell forming the housing of the inhaler.

Referring now to FIGS. 3a to 3e of the accompanying drawings, there is shown an inhaler 10 having a housing 11 formed from two shell portions 11a, 11b (see FIGS. 6 and 7), a cap 12 pivotally mounted to the housing 11 for rotation about an axis marked "C" (see FIGS. 5 to 7) from a closed position as shown in FIG. 4 in which the cap 12 covers and protects a mouthpiece 13 to a fully open position, as shown in FIGS. 3(b) to 3(d) and in a direction indicated by arrow "R" in FIG. 3(a), in which the mouthpiece 13 is exposed to enable a user to inhale a dose of medicament through the mouthpiece 13.

It should be noted that the cap is 'passive' in the sense that it can be opened and closed freely without performing the function of indexing of the blister strip or causing a blister piercing member 15 depending from the mouthpiece 13 to pierce the lid of an aligned blister.

The cap 12 is rotated into its fully open position in the direction of arrow "R". An actuating lever 14 is revealed as soon as the cap 12 is rotated out of its closed position. The user then applies pressure to the actuating lever 14, so that it rotates in the direction indicated by arrow "S" in FIG. 3(b).

During initial rotation of the actuating lever 14 through a first portion of its stroke into the position as it is shown in FIG. 3(b), the strip is indexed so as to move an unused blister into alignment with the blister piercing member 15.

When the actuating member is rotated through a second portion of its stroke beyond the position shown in FIG. 3(b) and after having completed the first portion of its stroke, in the direction of arrow "T" in FIG. 3(c), the strip remains stationary but the mouthpiece 13 is now pivoted so that the blister piercing member 15 pierces the lid of the previously aligned blister.

Although reference is made to a blister piercing member 15, it will be appreciated that multiple openings are formed in the lid of the blister so that air can be drawn into the blister through one or some of those openings and flow out of the blister together with an entrained dose of medicament, through one or more other openings and via the mouthpiece into a patient's airway.

Once the actuating lever is in the position shown in FIG. 3(c), the user now inhales through the mouthpiece 13, as shown by arrows indicated by "U" in FIG. 3(d).

After inhalation, the user rotates the cap in the opposite direction, i.e. in the direction indicated by "V" in FIG. 3(e). During this movement, the cap 12 engages with the actuating lever 14 so that the actuating lever 14 also returns to its initial position as shown in FIG. 3(a), the strip remaining stationary during this return movement of the actuating lever 14.

As mentioned above, the cap 12 is passive, although it does perform the function of re-setting the actuating member back to its original position in the event that the actuating lever is depressed prior to closing the cap.

As previously mentioned, the inhaler of the invention has an indexing mechanism that has previously been described with reference to WO2009/092652 A1. This aspect of the inhaler of the invention will now be described in detail with reference to FIGS. 8 to 13a. Although the drawings show a slightly different arrangement, in which an actuator 54 takes the place of a drive gear 16 attached to the drive coupling member 57 in the present invention, the principle remains the same as the actuator 54 and the drive gear are both rotated to index the strip. Therefore, rotation of the drive gear 16 performs the same function as rotation of the actuator 54 referred to in the description of FIGS. 8 to 13a below.

Figure 8:
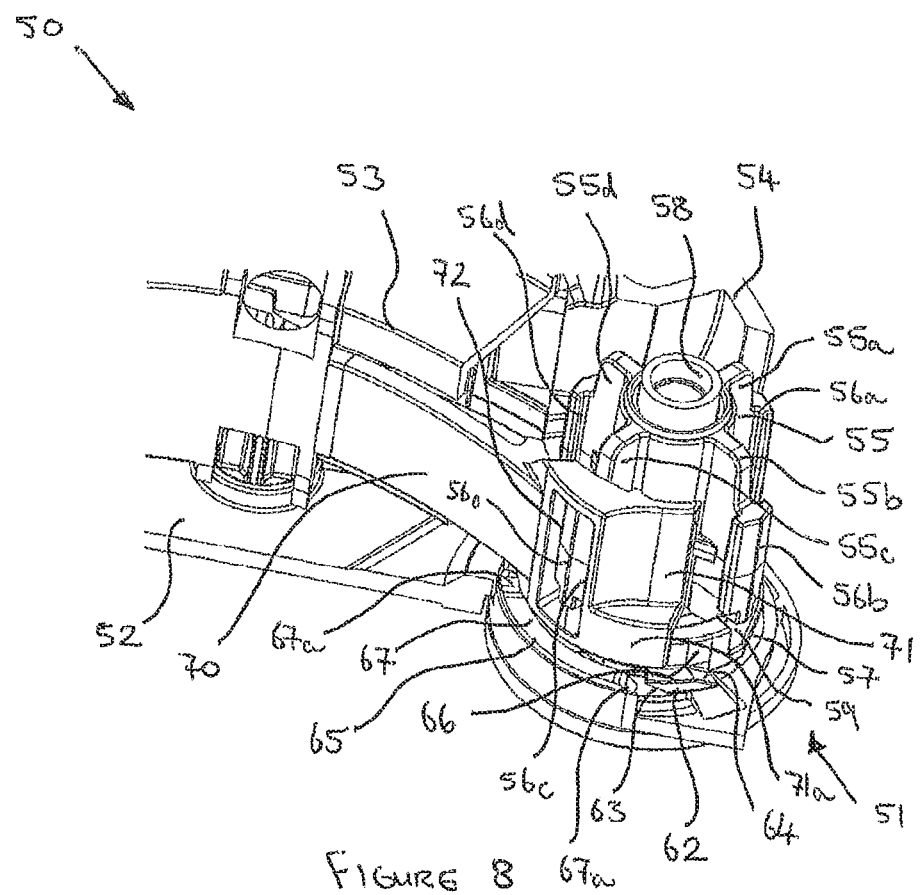
FIG. 8 is a partial perspective view of the blister strip indexing mechanism for use in the inhaler of the invention.
Figure 9:
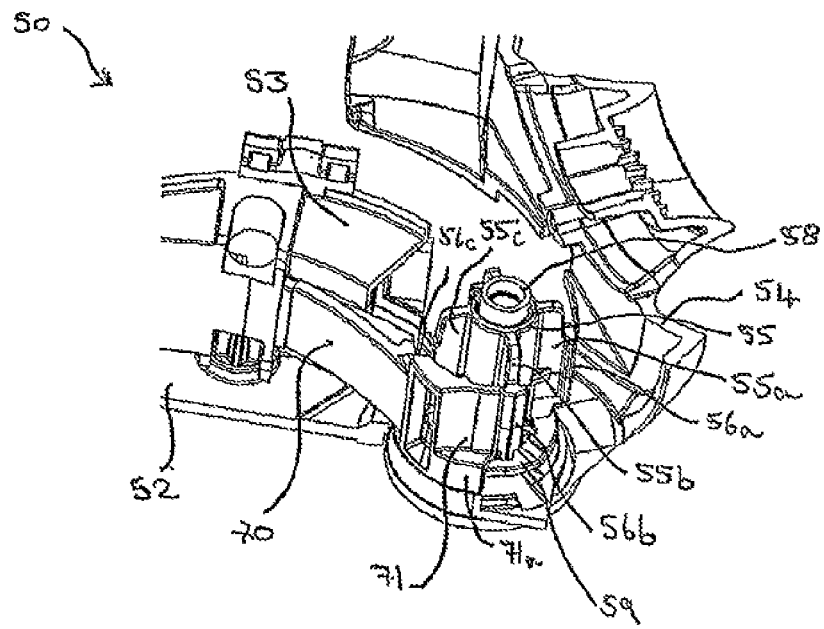
FIG. 9 is a partial perspective view of the blister strip indexing mechanism shown in FIG. 8 following partial rotation of the actuating lever into an intermediate position from its home position.
Figure 10:
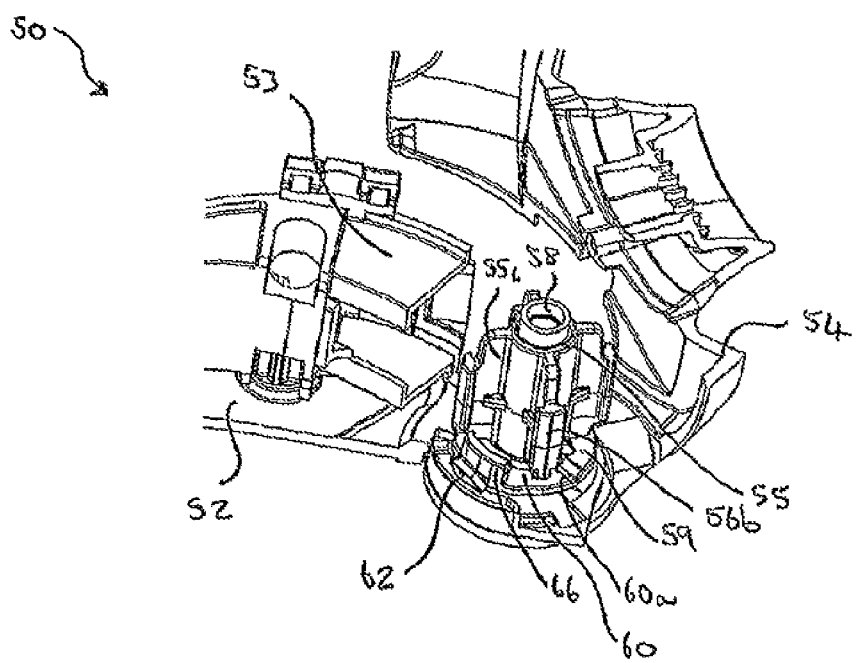
FIG. 10 is the same view as shown in FIG. 9, but without the optional cantilevered chassis arm.
Figure 11:
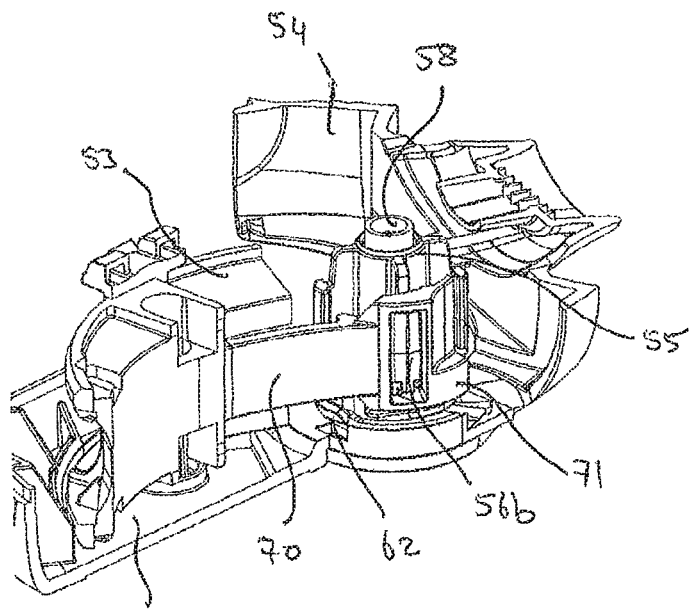
FIG. 11 is a partial perspective view of the blister strip indexing mechanism shown in FIGS. 8 to 10, after the actuating lever has been rotated to a point at which drive between the drive coupling and the actuator has disengaged.
Figure 12:
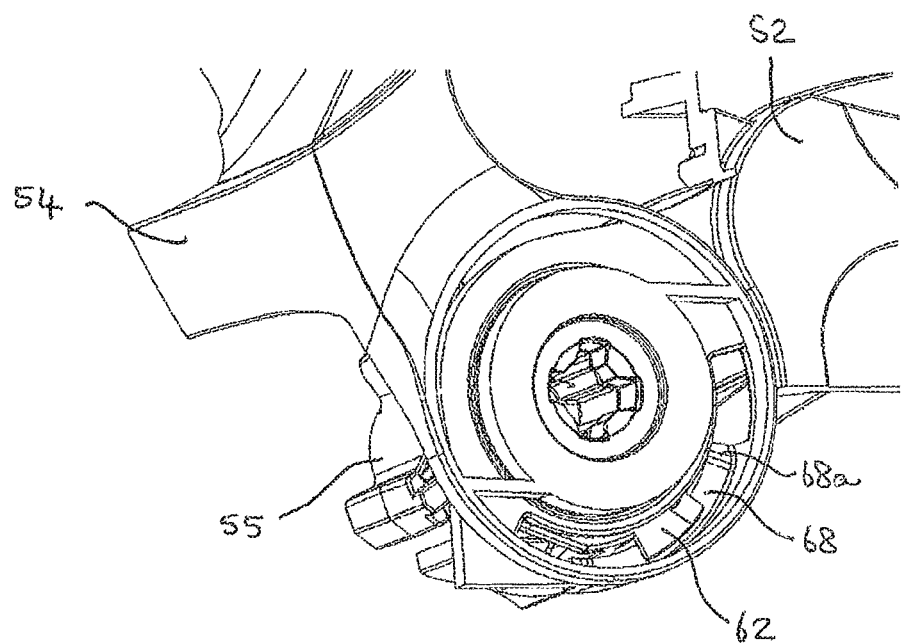
FIG. 12 is a partial perspective view of the opposite side of the indexing mechanism shown in FIGS. 9 to 11.
Figure 13A:
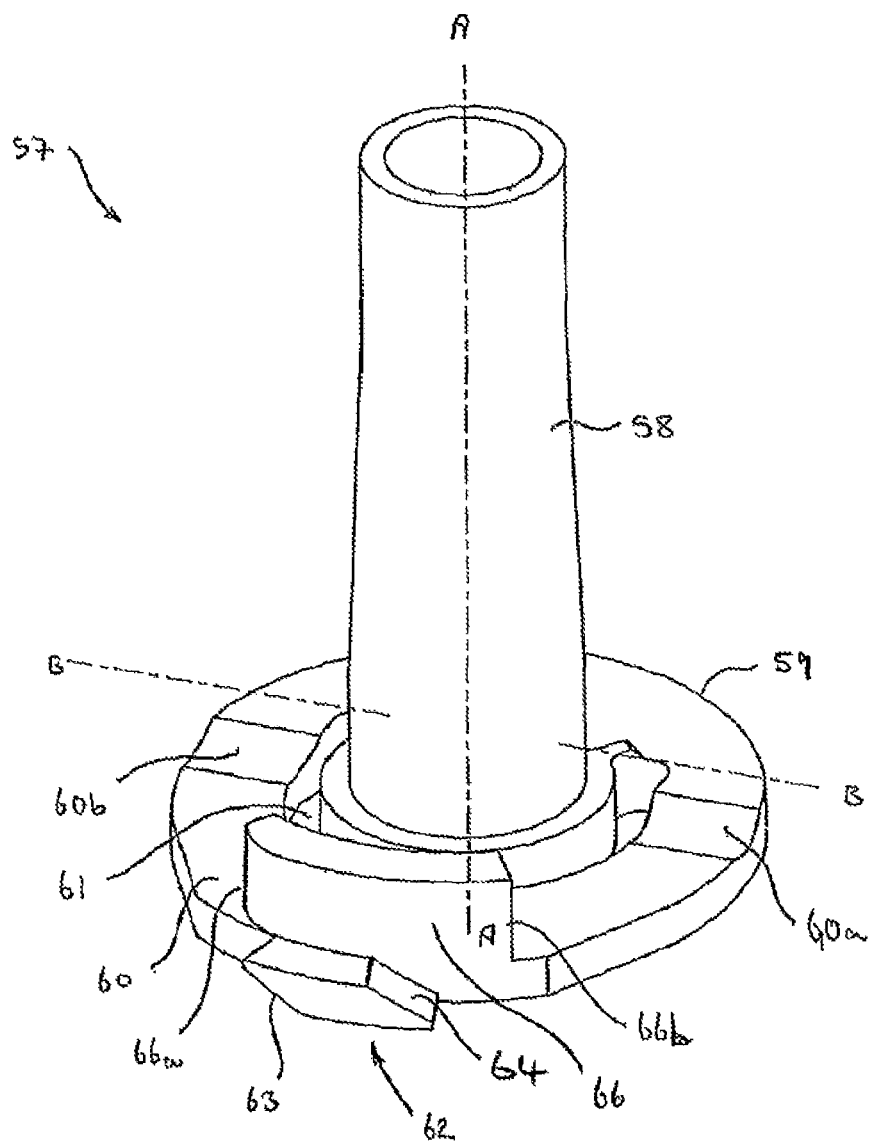
FIG. 13*a* is a perspective view of the drive coupling used in the indexing mechanism of the inhaler shown in FIGS. 9 to 12.
Figure 13B:
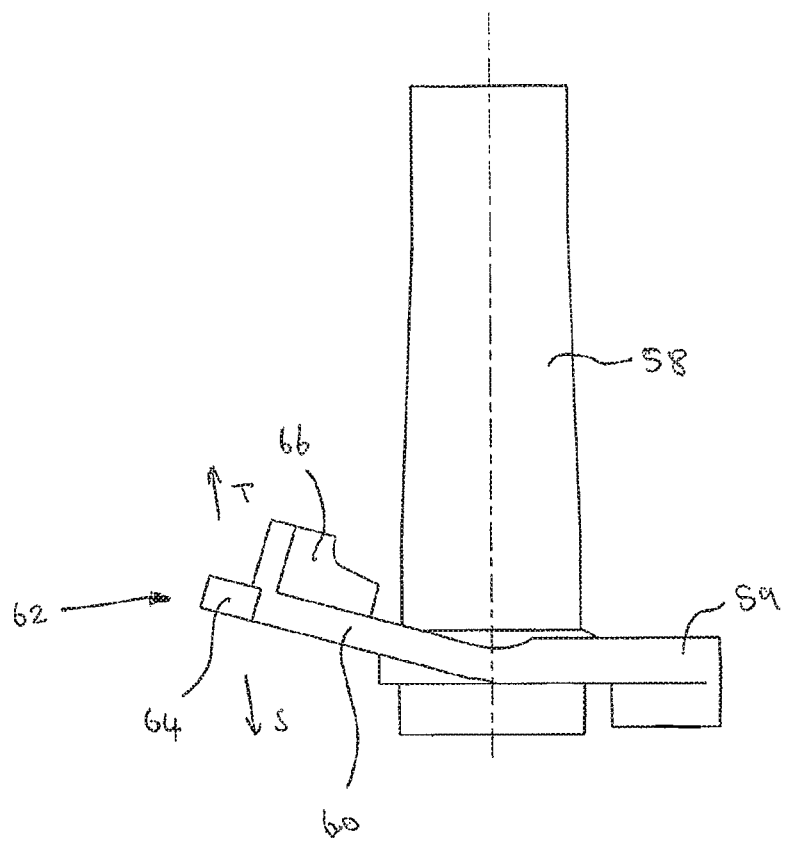
FIG. 13*b* is a side view of the drive coupling illustrated in FIG. 13*a* in which the flexible flange portion has been deflected in a direction "T" towards the shaft or, towards an indexing wheel mounted on that shaft.
Figure 14:
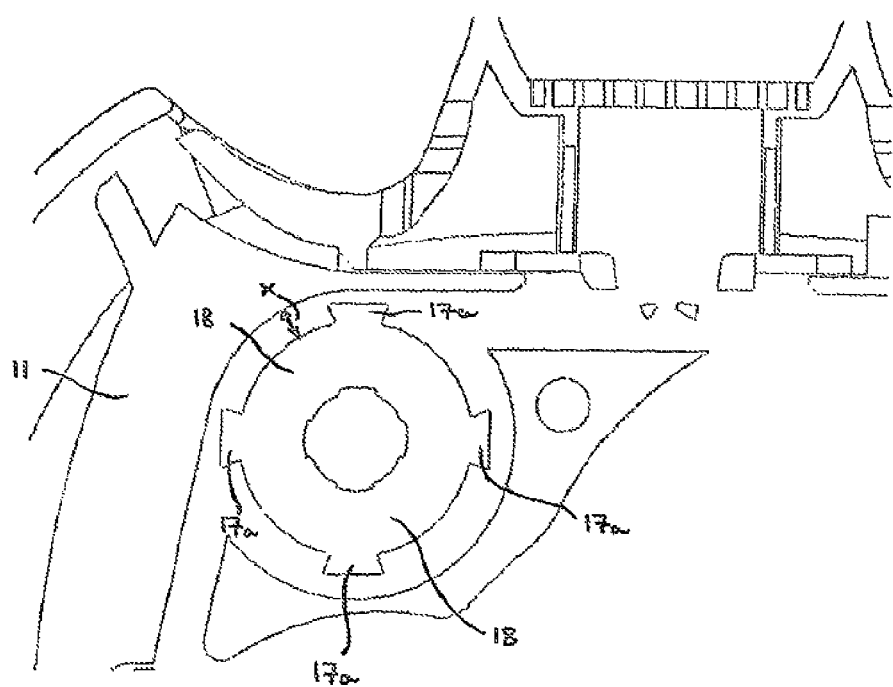
FIG. 14 is a partial view of the inhaler according to the invention showing the form and position of the indexing wheel that may be used in order to crush used blisters as they pass around the indexing wheel.

Referring now to FIG. 8, there is shown a partial perspective view of an inhalation device 50 comprising an indexing mechanism 51.

Figure 1:
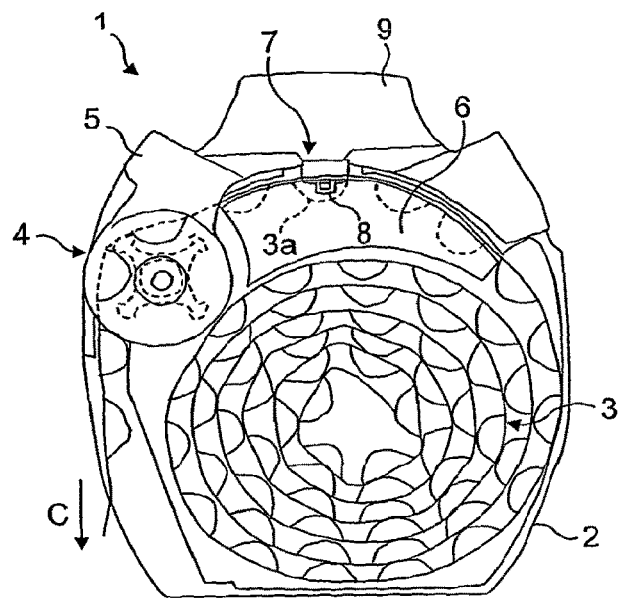
FIGS. 1 and 2 are side views of a conventional inhalation device to show how a strip is driven to sequentially move blisters into alignment with a blister piercing element by movement of an actuator from the position shown in FIG. 1 to the position shown in FIG. 2 which drives an indexing wheel. A piercing head on the actuator pierces the lid of an aligned blister when the actuator is returned to its normal position, as shown in FIG. 1.
Figure 2:
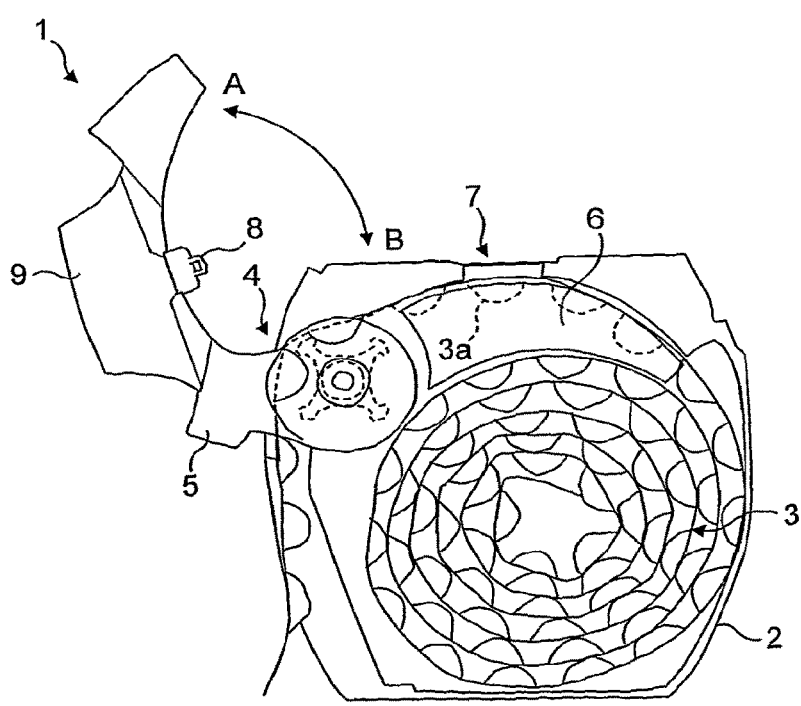

The indexing mechanism 51 includes an indexing wheel 55 comprising four vanes 55a,55b,55c,55d, each having an enlarged head portion 56a,56b,56c,56d. As is clear from reference to FIGS. 1 and 2, once a blister strip (not shown in FIGS. 8 to 14) has passed over the blister locating chassis 53, it passes around the indexing wheel 55. A blister locates in the space between two vanes 55a,55b,55c,55d so that, as the indexing wheel 55 rotates in response to rotation of the actuator 54, a vane 55a,55b,55c,55d engages a blister located between the vanes 55a,55b,55c,55d so as to drive the strip around the indexing wheel 55 to sequentially move each blister forward by a sufficient distance to move a fresh blister into alignment with a blister piercing element.

The indexing mechanism 51 includes a drive coupling member 57 (most clearly shown in FIGS. 13a and 13b) for selectively or temporarily coupling the actuator 54 to the indexing wheel 55 so that, when coupled, the indexing wheel 55 rotates in response to rotation of the actuator 54 to index the strip. The drive coupling member 57 comprises a shaft 58 defining an axis of rotation "A" (see FIGS. 13a and 13b) on which the indexing wheel 55 is rotatably received so that it can rotate freely about the shaft 58 about said axis of rotation "A". The actuator 54 is fixedly attached to the drive coupling member 57 (the gear drive would also be fixedly attached to the drive coupling member 57) so that the drive coupling member 57 rotates together with the actuator 54 at all times. In the embodiment illustrated and described with reference to FIGS. 8 to 12, the actuator 54, drive coupling member 57 and indexing wheel 55 are all mounted coaxially for rotation about the same axis "A". However, it will be appreciated that in the embodiment of FIG. 7, the mouthpiece 13 and actuating lever 14 are not coaxially mounted with Axis 'A'.

The drive coupling member 57 has a circular flange 59 that extends radially from one end of the shaft 58. A portion 60 of the flange is cut-away (see arcuate opening 61 in FIG. 13a) over an angle of approximately 180 degrees where the flange 59 joins the shaft 58 so that this portion 60 of the flange 59 is not directly attached to the shaft 58 but only to the remaining portion of the flange 59 at each of its ends 60a,60b. As a result, this portion 60 of the flange 59 is flexible relative to the rest of the flange 59 and can be deflected out of the plane of the flange 59 that extends at right angles to the axis of the shaft, in an axial direction (indicated by "T" and "S", in FIG. 13b) either towards or away from the shaft 58 or, more importantly, towards or away from the indexing wheel 55 which is mounted on the shaft 58, when force is applied to it. This flexible flange portion 60 hinges about an axis B which intersects the axis A of the shaft 58 and actuator 54 but extends at right angles to it. The drive coupling member 57, or at least the flange 59, is made from a resilient material so that when the deflected flexible flange portion 60 is released, it returns to its neutral, unstressed position, in which it lies coplanar with the remaining fixed portion of the flange 59.

The flexible flange portion 60 has an integrally formed flange deflecting dog 62 projecting radially from its circumferential edge. The flange deflecting dog 62 has first and second angled engaging faces 63,64 on opposite sides. When the drive coupling member 57 is rotated in response to rotation of the actuator 54 in one direction, one of the first or second angled engaging faces 63,64 cooperate with a fixed formation 65 on the housing 52 to cause the flexible flange portion 60 to deflect in a first direction. When the drive coupling member 57 is rotated in the opposite direction, the other angled engaging face cooperates with the formation 65 on the housing 52 to cause the flexible flange portion 60 to deflect in a second, opposite direction, as will be explained in more detail below.

The flexible flange portion 60 also has an arcuately shaped indexing wheel drive dog 66 that upstands in an axial direction from its surface towards the indexing wheel 55 in the same direction as the shaft 58 and extends partially around the circumference of the flexible flange portion 60. As will now be explained in more detail below, an end face 66a (see FIG. 13a) of the indexing wheel drive dog 66 engages a vane 55a,55b,55c,55d of the indexing wheel 55 when the flexible flange portion 60 has been deflected in a first direction, as indicated by arrow "T" in FIG. 13b (the flange portion 60 is shown in its deflected position in FIG. 13b), so that the indexing wheel 55 is driven together with the drive coupling member 57.

As mentioned above, the flange deflecting dog 62 engages a formation 65 on the housing 52 when the drive coupling member rotates in response to rotation of the actuator 54 so as to flex the deflectable portion 60 of the flange 59. This formation 65 comprises first and second arcuately shaped tracks or paths 67, 68 positioned one above the other or spaced from each other in the axial direction. The surface of the innermost track 67 is visible in FIG. 8. The lower or outermost track 68 is located beneath it and is visible in FIG. 12. The ends of the tracks 67a, 68a have angled faces for reasons that will become apparent.

When the actuator 54 (or the drive gear) is rotated in a first direction, the drive coupling member 57 rotates together with it and the first outwardly facing angled surface 63 on the flange deflecting dog 62 contacts the angled face 67a of the innermost track 67. Further rotation of the drive coupling member 57 causes the flange deflecting dog 62 to ride up onto the surface of the innermost track 67 thereby deflecting the flexible flange portion 60 inwardly, i.e. in a direction into the housing 52 or towards the shaft 58 and the indexing wheel 55.

When the flexible flange portion 60 has been deflected inwardly in the direction of arrow T, further rotation of the drive coupling member 57 causes the indexing wheel drive dog 66 to engage a vane, which as shown in FIG. 8 is vane 55c, of the indexing wheel 55 so that the indexing wheel 55 rotates together with the drive coupling member 57 and drive to the indexing wheel 55 is engaged.

When the end of the innermost track 67 has been reached, the flange deflecting dog 62 falls off the surface of the track 67 and the resilience of the flexible flange portion 60 causes it to return to its original unstressed or neutral position. When the drive coupling member 57 is rotated further, the indexing wheel drive dog 66 no longer engages with the vane 55c of the indexing wheel 55 and instead passes beneath it so the indexing wheel 55 remains stationary. Therefore, drive to the indexing wheel 55 is disengaged, despite continued rotation of the actuator 54 in the same direction.

When the actuator 54 is rotated back in the opposite direction towards its home position, the second inwardly facing angled surface 64 of the flange deflecting dog 62 now contacts the lower or outermost track 68 so that the flange deflecting dog 62 now rides onto the surface of that second track 68, thereby causing the flexible flange portion 60 to deflect outwardly or in the opposite direction to the direction in which it was previously deflected. Engagement of the flange deflecting dog 62 with the outermost track 68 so as to deflect the flange portion 60 in the opposite direction, enables the drive coupling member 57 to rotate in the opposite direction without any drive to the indexing wheel 55. It will be appreciated that, if the flange portion 60 was not deflected in the opposite direction, the flange deflecting dog 62 would simply engage against the end of the formation 65 in the housing 52 when rotated back in the opposite direction, thereby preventing rotation in the opposite direction or, the flange deflecting dog 62 would travel back over the innermost track 67 deflecting the flexible flange portion 60 in the same direction causing the opposite end 66b of the indexing wheel drive dog 66 to engage with a vane 65b of the indexing wheel 65 thereby driving the indexing wheel 65 backwards rather than leaving it stationary with no drive engaged. Therefore, it is necessary to ensure that the flexible flange portion 60 is deflected in the opposite direction so that there is no drive to the indexing wheel during rotation of the coupling member 67 in the opposite direction.

When the flange deflecting dog 62 reaches the end of the outermost track 68, the flexible flange portion 60 returns to its original unstressed or neutral position, due to its resilience.

It will be appreciated that the extent of rotation of the indexing wheel 55 relative to the extent of rotation of the actuator 54 may be controlled by altering the circumferential length of the inner and outer tracks 67,68. If the tracks are made longer, the flexible flange portion 60 will be deflected for a greater proportion of the angle through which the actuator 54 is rotated and so the indexing wheel drive dog 66 will be engaged with the indexing wheel 55 to rotate the indexing wheel 55 throughout that angle. If required, the tracks 67,68 could be made sufficiently long so that the indexing wheel 55 rotates during rotation of the actuator 54 through its entire angle of movement in one direction. Alternatively, the tracks 67,68 could be made shorter to reduce the angle through which the actuator 54 and indexing wheel 55 rotate together. Ideally, the track length can be selected so that the indexing wheel 55 is rotated through a sufficient angle to move the next, unused blister, into alignment with the blister piercing element.

The further rotation of the actuator 54 (the gear drive) causes the mouthpiece to rotate so that the blister piercing member pierces the lid of a blister that has just been moved into alignment with the blister piercing element.

It will be appreciated that the indexing mechanism 51 is designed to enable a stroke to be aborted when the actuator 54 or cap has been rotated through an angle which is sufficient to cause initial indexing of the strip but which is not such that the drive to the indexing wheel 55 has disengaged, i.e. a position in which the flange deflecting dog 62 has not reached the end of the innermost track 67. If the stroke is aborted and the actuator 54 returned to its original position before drive to the indexing wheel 55 has disengaged (or the drive gear rotated back to its initial position), the strip will be driven backwards into its original position as a rear surface 66b of the indexing wheel drive dog 66 will engage a preceding vane 55b to drive the indexing wheel 55 in the opposite direction.

The indexing mechanism 51 also includes optional means for locking the indexing wheel 55 to prevent its rotation between indexing steps and means for temporarily releasing that lock to allow rotation of the indexing wheel 55 when driven by the indexing wheel drive dog 66. The lock also improves positional accuracy of the strip and, more specifically, the next blister to be pierced. This locking arrangement will now be described in more detail below, although it should be noted that the locking mechanism can be omitted altogether.

The blister location chassis 53 may optionally comprise a resiliently flexible cantilever arm 70 that extends from the body 53 of the chassis towards the indexing wheel 55. The free end of the cantilever arm 70 has an enlarged head portion 71 comprising a letterbox shaped slot, window or opening 72 in which the head 56c of a vane 55c of the indexing wheel 55 is located. The opening 72 is dimensioned such that the head 56c of the vane 55c (as shown in FIG. 8) is a snug fit therein so that rotation of the indexing wheel 55 is prevented. In the normal or home position of the actuator 54, the head 56c of a vane 55c is located in said opening 72 in the cantilever arm 70 of the chassis 53 so that rotation of the indexing wheel 55 is prevented.

When the actuator 54 is rotated and the flange deflecting dog 62 engages the innermost track 67 so as to deflect the flexible portion of the flange 60 inwardly towards the indexing wheel 55, the indexing wheel drive dog 66 initially engages with a protrusion 71a extending from an inner side of the enlarged head 71 on the cantilever arm 70 of the chassis 53 so that the cantilever arm 70 is deflected outwardly, away from the indexing wheel 55, to free the head 56c of the vane 55c from the slot 72, thereby unlocking the indexing wheel 55. Only once the indexing wheel 55 has been released by the indexing wheel drive dog 66 pushing the cantilever arm 70 away from the indexing wheel 55 does the indexing wheel drive dog 66 subsequently engage a vane 55c of the indexing wheel 55 so that further rotation of the drive coupling member 57 rotates the indexing wheel 55.

Prior to the flange deflecting dog 62 falling off the end of the innermost track 67 and the flexible flange portion 60 returning to its undeflected state due to its resilience, the indexing wheel drive dog 66 no longer pushes against the cantilever arm 70 and so the cantilever arm 70 is free to move back towards the indexing wheel 55. As the cantilever arm 70 is free to move back just prior to rotation of the indexing wheel 55 being completed, the cantilever arm is prevented from moving all the way back by the head 56b of a following vane 55b which contacts the cantilever arm 70. During further rotation of the indexing wheel, the head 56b slides across the cantilever arm and then drops into the opening 72 thereby allowing the cantilever arm 70 to move all the way back and locking the indexing wheel 55 in position prior to any further rotation of the drive coupling member 57 in response to continued rotation of the actuator 54.

On the return stroke of the actuator 54, it will be appreciated that deflection of the flexible flange portion 60 in the opposite direction, i.e. in a direction away from the indexing wheel, also ensures that the indexing wheel drive dog 66 clears the chassis arm 70 and so the indexing wheel 55 is not unlocked, thereby preventing any rotation of the indexing wheel 55 during the return stroke.

The blister strip drive member or indexing wheel 55 of the invention may take a slightly different form to that described with reference to FIGS. 8 to 13b, although the principle still remains the same. In particular, the indexing wheel 55 may be used to squeeze the used blister cavities as they pass around it, thereby at least partially crushing them. This is achieved by enlarging the axle or hub 18 of the indexing wheel so that the distance (X in FIG. 14) between the hub and the casing or wall of the device 11, or a component fixed to the casing 11, is less than the maximum height of a blister cavity. As the blister cavities are entrained between the spokes 55a of the indexing wheel 55, onward rotation of the wheel 55 causes the cavities to be at least partially squashed or sandwiched between the enlarged hub 18 of the indexing wheel 55 and the casing 11 of the device. The advantage of at least partially crushing the empty blister cavities is that they then take up less space when coiled within the used blister chamber of the device as the coiled strip has a smaller diameter. Furthermore, a natural curvature is imparted to the strip, both as a result of being fed around the blister drive wheel and also as a result of the crushing of the blister cavities. This encourages the used portion of the strip to coil more readily. It is also apparent that, when the blister cavities have been crushed, the cavity is more resilient to denting at the point at which the spoke of the blister drive wheel contacts the strip, i.e. at the root where the blister cavity meets the remainder of the strip. Therefore, a more positive and precise drive of the strip is achieved when the blisters have been crushed.

As mentioned above, the drive coupling member 57 of the inhaler of the present invention is modified in that the drive gear 16 is attached thereto in place of the actuator 54 so that the drive coupling member 57 rotates in response to rotation of the drive gear 16. It is also envisaged that the drive gear 16 may be moulded integrally with the drive coupling member 57.

Figure 7:
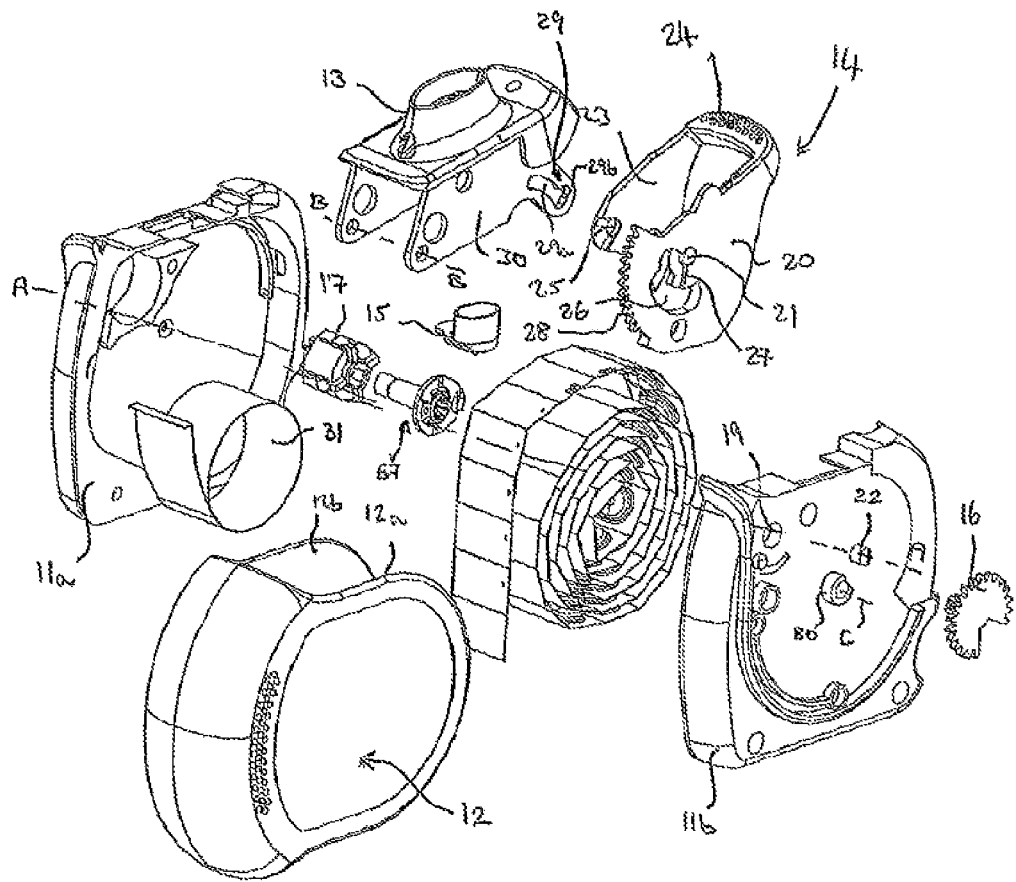
FIG. 7 is an exploded perspective view showing the individual components of the inhaler according to the invention.

It will be apparent from FIG. 7, that the drive coupling member 57 extends into an opening 19 in a side wall of the shell 11b of the housing 11 and the drive gear 16 is coupled thereto so that it is disposed on the outside surface of said side wall, only the drive coupling member 57, the blister strip drive wheel 17 and the blister strip itself, being received within the housing between the shell portions 11a, 11b.

Figure 15:
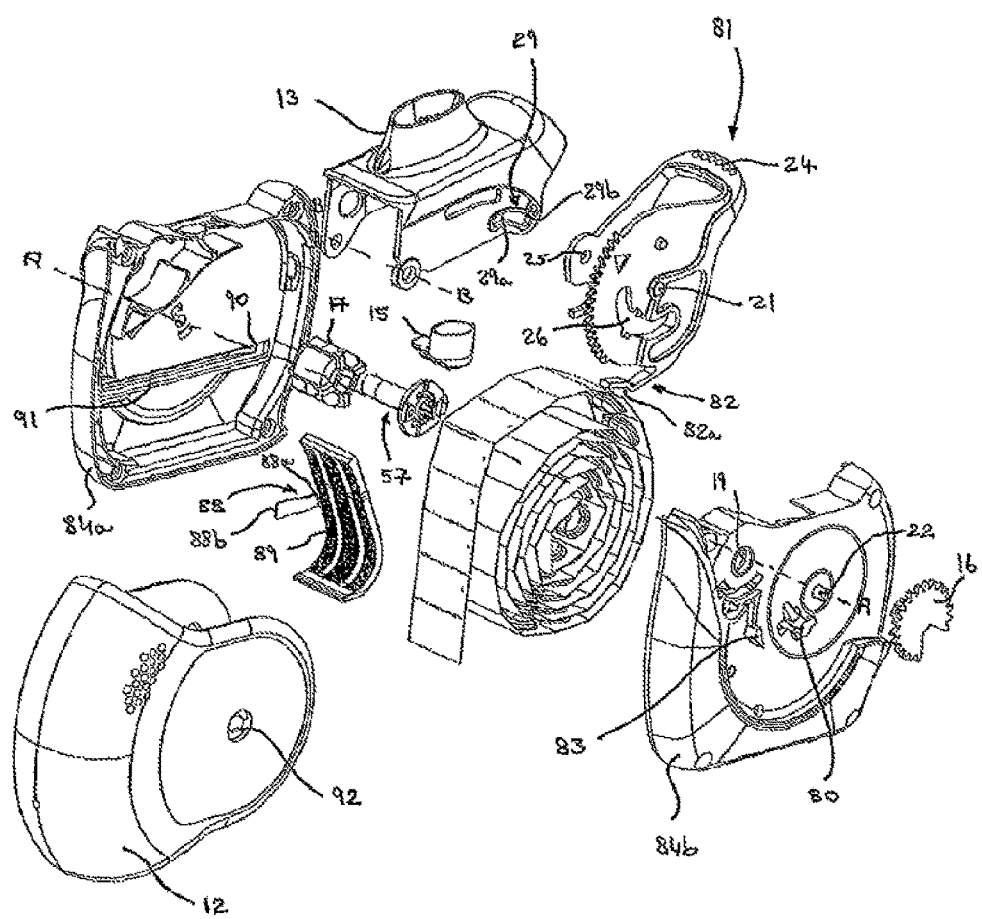
FIG. 15 is an exploded perspective view showing the individual components of the inhaler according to another embodiment of the invention.

The actuating lever 14 has a first plate-like portion 20 that extends across the outside surface of the shell 11b and has a hole 21 therein to receive a boss 22 upstanding from said surface, to pivotally mount the actuating lever 14 to the shell 11 for rotation about a second axis (A-A in FIGS. 7 and 15). The actuating lever 14 may also have a second plate-like portion 23 that is parallel to and spaced from the first portion 20 by an actuating button 24. The second plate-like portion extends across the opposite surface of the shell 11a and also has a hole 25 to engage with a corresponding boss upstanding from said opposite surface so as to pivotally couple the actuating member 14 to the shell 11 with the actuating button extending between the plates 20,23 and opposite surfaces of the shell portions 11a, 11b.

The first plate 20 has a further aperture 26 therein and the cap 12 is pivotally mounted to the outer shell portion 11b by a coupling such as a boss 80 upstanding from a surface of the shell portion 11b that locates in a corresponding recess (not shown in FIG. 7, but see hole 92 in FIG. 15) in the cap 12, for rotation of the cap 12 about a third axis. The boss 80 extends through the aperture 26 in the actuating member 14. The aperture 26 is arcuately-shaped and has the second axis as its centre so that, when the actuating lever 14 is rotated about the second axis, the boss 80 travels within the aperture 26 without engaging the actuating member 14, and so the cap 12 remains stationary. The actuately-shaped aperture 26 acts as a clearance hole for the pivotal attachment of the cap 12 to the shell 11b and so as to allow rotation of the actuating lever 14 about the second axis.

A drive member (not shown) extends from an inner surface of the cap 12. The drive member is located between, and spaced from, each of the second and third axes and extends towards the actuating lever 14 and the actuating lever 14 includes a wall 27 for engagement by said drive member when the cap 12 is rotated it about its third axis back towards its closed position and after the actuating member 14 has been rotated about its second axis. The drive member and wall 27 meet at a location between the second and third axes so that, upon further rotation of the cap 12 back towards its closed position, the drive member pushes against the wall 27. Pressure of the drive member against the wall 27 causes the actuating member 14 to rotate back into its original position, together with the cap 12 into its closed position.

The cap 12 and actuating lever 14 are configured so that, when the cap 12 is in its closed position and the actuating lever 14 has returned to its initial position, the cap 12 overlies the actuating button 24 which is pressed by a user to operate the device. This prevents a user from attempting to operate the device by rotating the actuating member 14 prior to opening the cap 12.

The actuating member 14 has a gear segment, toothed region or element 28 that drivingly meshes with the gear drive 16 so that rotation of the actuating member 14 also causes rotation of the gear drive 16 and selective rotation of the blister strip drive member relative to the gear drive 16 whilst the actuating member 14 is rotated through the initial portion of its stroke, due to the indexing mechanism described above, so that the blister strip is initially driven to move the next blister into alignment with the blister piercing member 15. During further rotation of the actuating member 14 through the second portion of its stroke, the blister strip is prevented from moving as the drive coupling member 57 is de-coupled from the blister strip drive wheel 17. During rotation through the second portion of its stroke, the blister piercing member 15 carried by the mouthpiece 13 is rotated so that it pierces the aligned, and now stationary, blister.

A cam drive member (not shown) extends from the first plate 20 towards the second plate 23. The cam drive member is received in a cam groove or slot 29 formed in a peripheral wall 30 depending from the mouthpiece 13. As is apparent from FIG. 7, the cam groove or slot 29 has an arcuate portion 29a followed by a leg portion 29b at one end. It will be appreciated that the slot 29 may alternatively be provided in the actuating lever 14 and the cam drive member may extend from the mouthpiece 13 to achieve the same function.

During initial rotation of the actuating member 14 through the first portion of its stroke, the cam drive member slides along the arcuate portion 29 of the cam slot 29 without causing any movement of the mouthpiece 13, as the arcuate portion 29a of the cam slot 29 has the second axis as its radius. However, during subsequent rotation of the actuating member 14, the cam member reaches the leg portion 29b of the cam slot 29 and engages the side walls of the cam groove 29 so as to cause the mouthpiece 13 to rotate about a first axis B-B together with the actuating member 14 thereby pulling the blister piercing member 15, depending from the mouthpiece 13, into the aligned blister.

Although reference is made to a pivoting mouthpiece 13, it will also be appreciated that, in an alternative embodiment, the blister piercing member 15 may be pivotally attached to a mouthpiece 13 or mounted in a support or module that is pivotally attached to the mouthpiece 13. In these embodiments, the mouthpiece 13 itself remains stationary so that, in response to operation of the actuating member 14, the blister piercing member 15 pivots relative to the stationary mouthpiece 13 to puncture the lid of an aligned blister.

During rotation of the cap 12 from its open to its closed position, rotation of the actuating member 14 due to rotation of the cap 12 also causes rotation of the mouthpiece back to its original position as the cam member travels back along the cam slot 29b.

As shown in FIG. 7, a spiral element 31 is also optionally mounted within the housing 11 into which the used portion of the strip is fed.

Although a region is provided within the housing 11 to receive the used portion of the strip, it will be appreciated that the invention is also applicable to other inhalation devices (not shown) in which used blisters are not retained within the housing 11 but pass out through an opening (not shown) in the wall of the housing 11 for periodic detachment by a user.

Although piercing of an aligned blister only occurs after movement of the strip has stopped, it is envisaged that the mechanism could be configured so that de-coupling of the blister strip drive wheel 17 and the drive coupling member 57 only occurs after the blister piercing element 15 has pierced, or begun to pierce, the lid of a blister so that the piercing element is drawn across and through the lid of the blister as it enters it. This creates a larger hole relative to the size of hole created when the strip is stationary prior to being puncturing by the blister piercing element. A larger hole can advantageously ensure that all the drug dose is entrained and removed from the blister.

Figure 16:
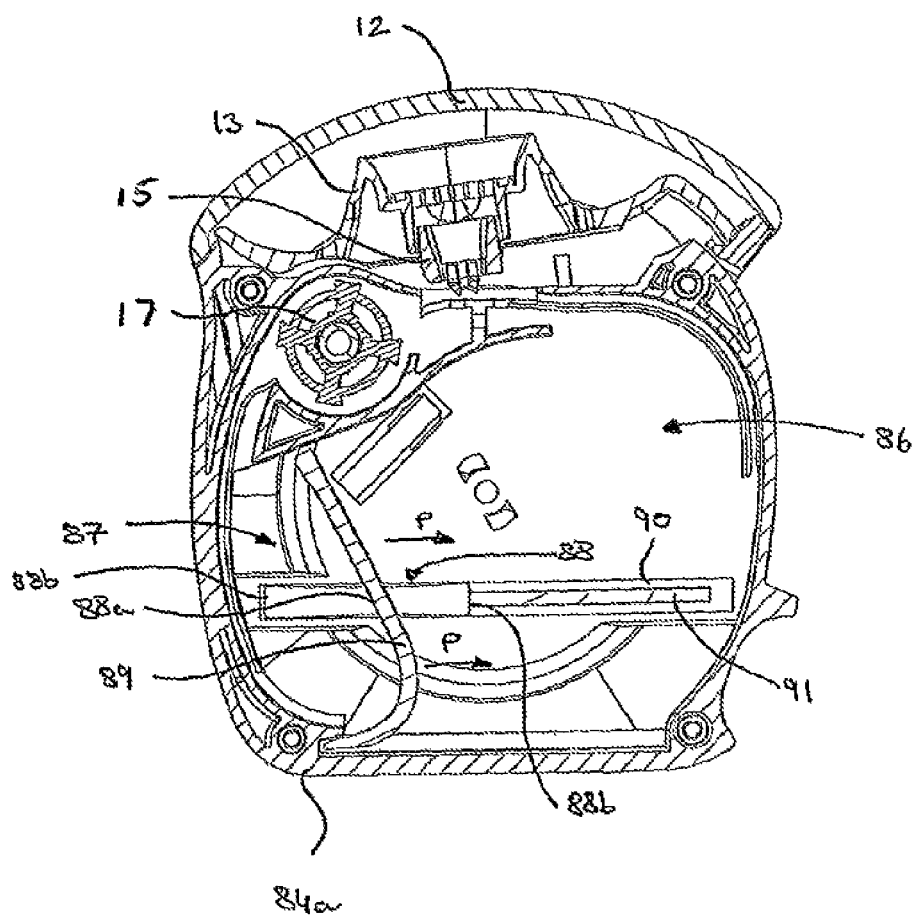
FIG. 16 is a cross-sectional side view of the inhaler shown in FIG. 15.

A modified embodiment is shown in FIGS. 15 and 16. This embodiment is similar to the previous embodiment and functions in the same way but additionally includes a detent mechanism for holding the actuating lever 81 at the end of its stroke so that a small force must be applied to it to overcome the hold placed on it by the detent mechanism and allow the actuating lever 81 to return to its initial position. The detent mechanism includes a cantilever 82 that extends from the actuating lever 81 and has a kinked region 82a which engages with a pawl 83 on the shell portion 84b as the actuating lever 81 approaches the end of the second portion of its stroke, so that the cantilever 82 is resiliently deformed and as it rides over the kinked region 82a and springs back to its original shape once the pawl 83 has cleared the kinked region 82a. When the actuating lever 81 is rotated back towards its initial position, sufficient force must initially be applied to the actuating lever 81 so that the cantilever 82 is deformed by the pawl 83 and rides back over it. In addition to providing a slight resistance to initial movement of the actuating lever 81, it also generates an audible 'click' as the end of the second portion of the stroke of the actuating lever 81 is reached and so provides an audible signal to the user that the end of the travel of the actuating lever 81 has been reached.

This embodiment also includes a rigid dividing wall 85 that separates the interior of the housing into an unused and used blister chamber 86,87 (see FIG. 16). The wall 85 is slideably mounted within the shell portion 84a of the housing so that, as more of the blisters are used, the force of the used coil of blisters in the used blister chamber 86 presses against the wall 85 and pushes it in the direction indicated by arrow 'P' in FIG. 16, to enlarge the space for the used blisters and reduce the space previously occupied by the unused blisters.

The sliding wall 85 comprises an elongate foot 88 which is attached to and integrally formed with a baffle 89 that divides the compartment. An approximate central region 88*a* of the foot 88 is attached to the baffle 89 so that it extends in opposite directions on either side of the baffle 89. The foot 88 is slideably received in a recess 90 formed in a wall of the housing and is wider at its ends 88*b* than in its centre 88*a* where it joins the baffle 89 so that contact with the walls of the recess 90 is primarily made with the wider ends 88*b* of the foot 88. A deeper, narrower recess 91 may extend deeper into the wall within the first recess 90 to receive a strengthening rib (not shown) depending from the underside of the foot 88.

As indicated above, the blister strip drive wheel 17 is rotatably mounted in the chamber to sequentially move each blister into a position in which it can be opened, preferably using a blister piercing element that punctures the lid of an aligned blister. However, the drive gear 16, which is driven to rotate the blister strip drive wheel 17, is disposed on the outside of the housing remote from the chamber in which the blister strip and blister strip drive wheel 17 are received. Similarly, the actuating lever 14 is disposed on the outside of the housing and is remote from the chamber. The drive gear segment or element 28 on the actuating lever 14 is therefore also on the outside of the housing, remote from the chamber. This has the advantage that any loose powder dose contained in the chamber is substantially prevented from contacting the gear segment 28 and the drive gear 16, which could increase friction and be detrimental to satisfactory blister indexing.

The respective drive gears namely, the drive gear 16 and the gear segment 28, are disposed between the housing 11 and the cap 12 so as to be enclosed by said cap 12 which includes portions 12*a*,12*b* that extend across respective side wall surfaces of the housing 11. This means that the drive gear 16 and the gear segment 28 are disposed between one of said side wall surfaces and one of said cap portions 12*a*,12*b*.

The drive gear 16 is connected to the blister strip drive wheel 17, via the drive coupling member 57, through the aperture 19 in the side wall of the housing.

It will also be appreciated that the mouthpiece is mounted to the outside of the housing, said peripheral wall 30 extending from opposing edges extending across respective side wall surfaces on the outside of the housing remote from the chamber. The peripheral walls are pivotally mounted to the side wall surfaces of the housing and are covered by a portion 12*a* of the cap 12.

A further modified embodiment will now be described with reference to FIGS. 17*a* to 17*f*. This embodiment is similar to the previous embodiments and so like components will not be described again. The inhaler of FIGS. 17*a* to 17*d* is additionally provided with a shutter 100 (see FIGS. 17*e* and 17*f*) that blocks the mouthpiece 13 when the mouthpiece 13 is in its raised position, but which pivots as the mouthpiece 13 is pulled downwardly in response to pressure on the actuating lever 14, 81 to pierce a blister so that the mouthpiece 13 is opened to allow a dose to pass therethrough when a patient inhales.

Figure 17A:
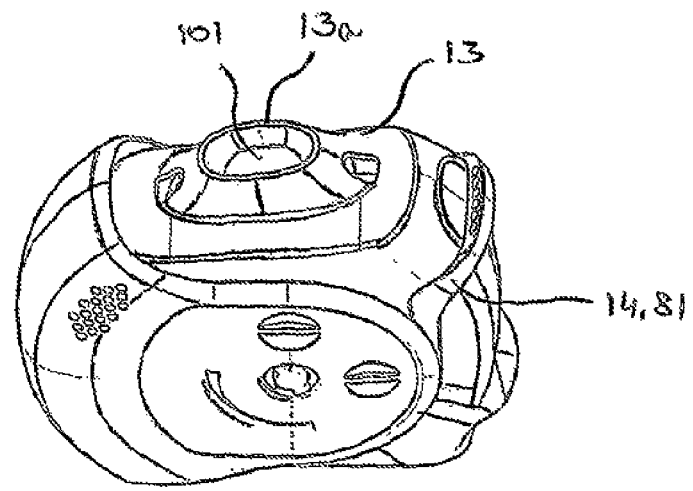
FIGS. 17a to 17f illustrate a further modified embodiment of the inhaler according to the invention that incorporates a shutter to block the mouthpiece.
Figure 17B:
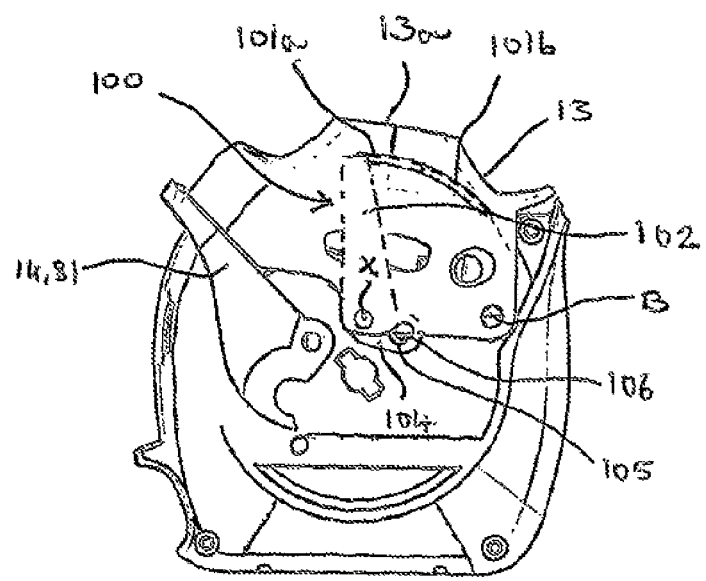

A top perspective view of the inhaler according to this embodiment can be seen in FIG. 17*a*. A corresponding side elevational view is shown in FIG. 17*b*, but with the cap 12 removed for clarity. In FIG. 17*a*, the cap 12 has been pivoted into its open position but the actuating lever 14, 81 has not yet been activated. As is visible in FIG. 17*a*, the mouthpiece 13 is blocked by a shutter portion 101 of a shutter component 100 which is visible through the mouthpiece opening 13*a*.

Figure 17C:
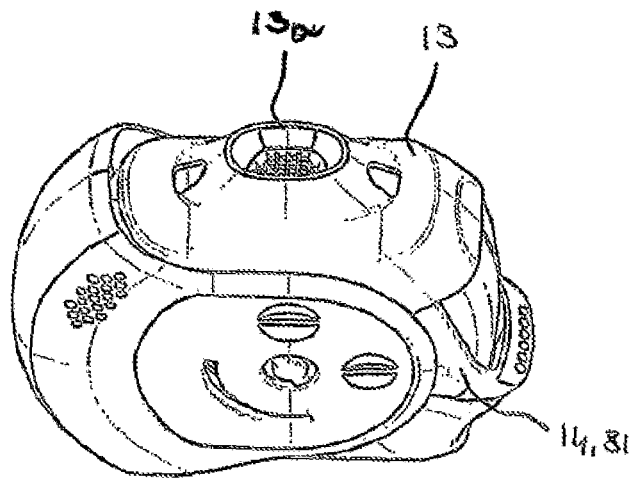
Figure 17D:
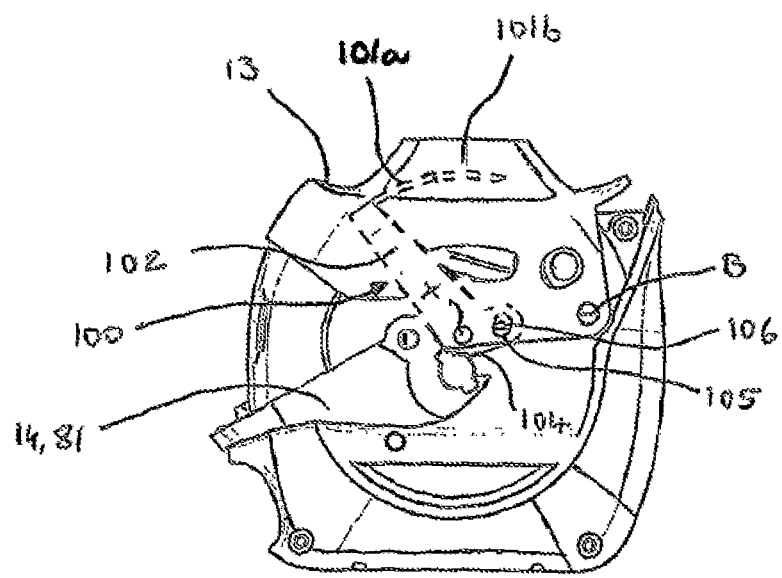
Figure 17E:
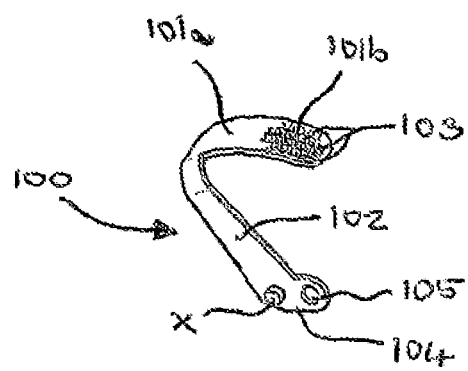
Figure 17F:
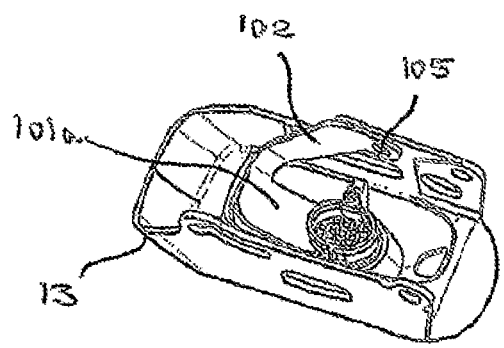

A top perspective view of the inhaler according to the embodiment can also be seen in FIG. 17*c*, together with a corresponding side view in FIG. 17*d* (with the cap 12 removed for clarity). However, in these views, the actuating lever 14, 81 has been pivoted through the full extent of its stroke so that the mouthpiece 13 has been driven downwardly and rotated about its pivot 'B'.

With reference to FIGS. 17*b* and 17*d*, it will be appreciated that the shutter 100 is represented in dashed lines to indicate that it is positioned beneath the mouthpiece 13 so that it is situated between the mouthpiece 13 and the casework 11, and so only part of the shutter portion 101 is visible to a user through the mouthpiece opening 13*a*.

The shutter portion 101 extends from one end of a pivot arm 102 and is arcuate in shape. A first section 101*a* of the arcuate shutter portion 101, extending directly from the pivot arm 102, is solid so that it completely blocks the mouthpiece opening 13*a*, whereas a second section 101*b* of the shutter portion 101 that extends from the first section 101*a*, remote from the pivot arm 102 is provided with openings 103, that form a mesh for the passage of an entrained dose out of the mouthpiece 13 and into the patient's mouth, although it is envisaged that a separate, stationary mesh, could be formed integrally with the mouthpiece 13 below the first section 101*a*, in which case the second portion 101*b* of the shutter arm 101 is not required.

The opposite end 104 of the pivot arm 102, remote from the shutter portion 101, is pivotally mounted to the mouthpiece 13 for rotation about an axis 'X'. The end 104 has an enlarged region relative to the rest of the pivot arm 102 and which extends laterally from the pivot axis 'X'. A cam slot 105 is formed in the enlarged region to receive a fixed cam pin 106 upstanding from the casework 11. The cam pin 106 is free to slide within the slot 105.

The arrangement is such that, as the mouthpiece 13 rotates about its pivot axis 'B' in response to pressure applied to the actuating lever 14, 81, the shutter 100 also rotates about its axis 'X' due to the interaction between the fixed cam pin 106 and the cam slot 105. The shutter 100 is thereby rotated into its position shown in FIGS. 17*c* and 17*d*, in which the second portion 101*b* of the shutter portion 101 is aligned with the mouthpiece opening 13*a* to allow passage of an entrained dose through the mouthpiece opening 13*a*.

The shutter 100 rotates in the opposite direction when the mouthpiece 13 pivots back to its original position in response to the cap 12 being closed (due to rotation of the mouthpiece 13 in the opposite direction as driven by the cap 12), thereby moving the first shutter portion 101 back into the mouthpiece opening 13*a* and blocking the mouthpiece 13.

Once the shutter is no longer visible through the mouthpiece opening 13*a*, the dose is pierced and ready to be inhaled. The shutter 100 also provides further protection to the mouthpiece (in addition to the cap 12) against the ingress of dust or debris into the inhaler which may occur if, for example, the cap 12 was pivoted into its open position and the inhaler was left in this state, with the mouthpiece 13 revealed, prior to depression of the actuating lever 14, 81 to pierce an aligned blister.

As the shutter 100 is pivotally mounted to the mouthpiece 13 and not to the casework 11, the shutter portions 101*a*, 101*b* always retain the same distance to the mouthpiece opening irrespective of the rotational displacement of the mouthpiece 13 so that the arcuate shutter portions always remain in the same close clearance to corresponding surfaces on the mouthpiece 13.

Many modifications and variations of the invention falling within the terms of the following claims will be apparent to those skilled in the art and the foregoing description should be regarded as a description of the preferred embodiments of the invention only. For example, although reference is made to a "mouthpiece", the invention is also applicable to devices in which the dose is inhaled through the nasal passages. Therefore, for the purposes of this specification, the term "mouthpiece" should also be construed so as to include within its scope a tube which is inserted into the nasal passages of a patient for inhalation therethrough.

Furthermore, although the blister piercing member 15 is described as being attached to the mouthpiece so that the mouthpiece 13 and the blister piercing member rotate together, it is also envisaged that the mouthpiece itself could remain stationary and the blister piercing element 15 could be pivotally mounted to the mouthpiece 13 so that the blister piercing member 15 rotates relative to the mouthpiece 13 to pierce the lid of an aligned blister.

In another embodiment, the cap and the actuating member could be combined into a single component so that rotation of the cap also causes indexing of the strip and piercing of an aligned blister.

It will be appreciated that the inhaler of the invention may be either a passive or active device. In a passive device, the dose is entrained in a flow of air caused when the user inhales through the mouthpiece. However, in an active device, the inhaler would include means for generating a pressurised flow of gas or air through the blister to entrain the dose and carry it out of the blister through the mouthpiece and into the user's airway. In one embodiment, the inhaler may be provided with a source of pressurised gas or air within the housing.

The invention claimed is:

1. An inhaler comprising a housing defining a chamber to receive a strip having a plurality of blisters each containing a dose of medicament for inhalation by a user, a cap, an actuating member which has a gear element having teeth, and a blister strip indexing wheel rotatably mounted in the chamber to sequentially move each blister into a blister opening position, wherein the cap and the actuating member are combined into a single component and wherein the blister strip indexing wheel and the cap are coupled by a drive gear that cooperates with the gear element to effect rotation of the blister strip indexing wheel in response to rotation of the cap, said drive gear and gear element being disposed on an outside of the housing remote from the chamber.

2. The inhaler according to claim 1, wherein the housing has opposing side wall surfaces and the cap has portions that extend across respective side wall surfaces, said drive gear being disposed between one of said side wall surfaces and one of said cap portions.

3. The inhaler according to claim 1, wherein a blister piercing member is immovably attached to a mouthpiece and the mouthpiece is pivotally mounted to the housing about a first axis so that the mouthpiece pivots, together with the blister piercing member, about said first axis in response to rotation of the cap about a second axis.

4. The inhaler according to claim 3, the drive gear and gear element being configured such that rotation of the cap gear element about the second axis through a first portion of its stroke moves a blister into alignment with the blister piercing member and, further rotation of the gear element about the second axis in the same direction, during a second portion of its stroke, causes rotation of the blister piercing member about the first axis so that the blister piercing member punctures a lid of an aligned blister.

5. The inhaler according to claim 1, wherein the blister strip indexing wheel comprises a plurality of spokes extending from a hub, the spokes being spaced from each other such that a spoke locates between the blisters as a blister strip passes around the blister strip indexing wheel to engage and drive a the blister strip as the blister strip indexing wheel rotates, the blister strip indexing wheel being positioned relative to a wall such that the distance between the hub and said wall is less than a height of the a blisters such that onward rotation of the blister strip indexing wheel causes the blisters to be at least partially squashed or, sandwiched between the hub and said wall.

* * * * *